United States Patent
Ferree

(10) Patent No.: US 6,494,883 B1
(45) Date of Patent: Dec. 17, 2002

(54) BONE REINFORCERS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 09/580,231

(22) Filed: May 26, 2000

(51) Int. Cl.⁷ .............................................. A61B 17/70
(52) U.S. Cl. ..................................... 606/61; 623/17.11
(58) Field of Search ......................... 623/16.11, 17.11, 623/17.16, 23.47, 23.51, 23.53; 606/61

(56) References Cited

U.S. PATENT DOCUMENTS

| | | | |
|---|---|---|---|
| 4,657,550 A | * 4/1987 | Daher | 606/61 |
| 4,878,915 A | 11/1989 | Brantigan | 623/17 |
| 5,015,247 A | 5/1991 | Michelson | 606/61 |
| 5,026,373 A | * 6/1991 | Ray et al. | 606/61 |
| 5,192,327 A | * 3/1993 | Brantigan | 606/60 |
| 5,292,332 A | 3/1994 | Lee | 606/213 |
| 5,336,223 A | 8/1994 | Rogers | 606/61 |
| 5,464,421 A | * 11/1995 | Wortrich | 606/213 |
| 5,571,192 A | * 11/1996 | Schonhoffer | 606/61 |
| 5,645,565 A | 7/1997 | Rudd et al. | 606/213 |
| 5,693,100 A | * 12/1997 | Pisharodi | |
| 5,702,455 A | * 12/1997 | Saggar | 623/17.15 |
| 5,814,084 A | * 9/1998 | Grivas et al. | 623/23.48 |
| 5,906,616 A | 5/1999 | Pavlov et al. | 606/61 |
| 6,045,554 A | * 4/2000 | Grooms et al. | 606/73 |
| 6,200,347 B1 | * 3/2001 | Anderson et al. | 623/11.11 |
| 6,214,050 B1 | * 4/2001 | Huene | 623/17.15 |
| 6,245,072 B1 | * 6/2001 | Zdeblick et al. | 606/61 |
| 6,261,586 B1 | * 7/2001 | McKay | 424/422 |
| 6,270,528 B1 | * 8/2001 | McKay | 623/16.11 |
| 2001/0020186 A1 | * 9/2001 | Boyce et al. | 623/17.16 |
| 2001/0034553 A1 | * 10/2001 | Michelson | 623/17.11 |
| 2001/0039458 A1 | * 11/2001 | Boyer, II et al. | 623/23.63 |
| 2001/0056302 A1 | * 12/2001 | Boyer, II et al. | 623/17.15 |

* cited by examiner

Primary Examiner—David O. Reip
Assistant Examiner—Daniel Jacob Davis
(74) Attorney, Agent, or Firm—Gifford, Krass, Groh, Sprinkle, Anderson & Citkowski, PC

(57) ABSTRACT

Existing bone dowels are improved through the use of rigid, preferably metallic end plates. The plates are positioned relative to the anterior and posterior end surfaces of the bone dowel, which may be an existing, modified, or a specially fabricated bone section. The completed structure may be inserted, removed, and positioned into the vertebrae in the same manner as existing devices, that is, by way of a threaded or frictional fit, just as the dowel being fortified. However, the use of the rigid endplates facilitates load sharing which helps to prevent graft fracture. In the preferred embodiment, the end plates are positioned against the end surfaces of the bone section through the use of a link member, which passes through the interior of the bone section and connects the end plates. One of the end plates may include a threaded bore, and one end of the link member may be threaded to receive the threaded bore of that end plate to hold it in place. The use of a link member allows a plurality of bone sections to be journaled onto the link member, with a disk of rigid, preferably metallic material to be interposed between each bone section. Alternatively, the end surfaces of the bone section may each include an aperture having an inside diameter, with each end plate having an outside diameter corresponding to the inside diameter of the apertures, enabling the end plates to be positioned against the end surfaces of the bone section through a frictional fit.

12 Claims, 5 Drawing Sheets

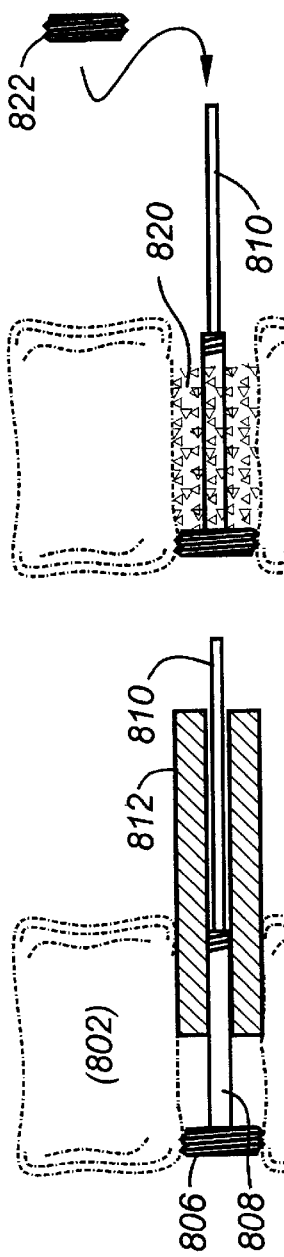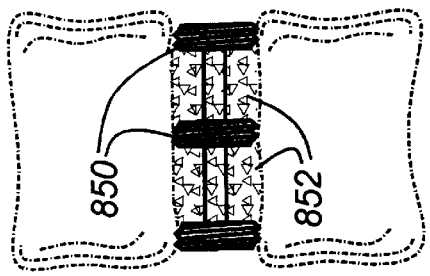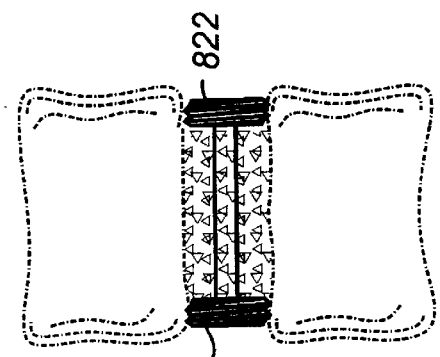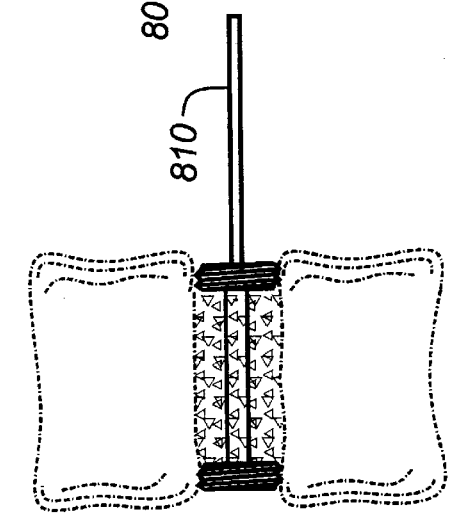

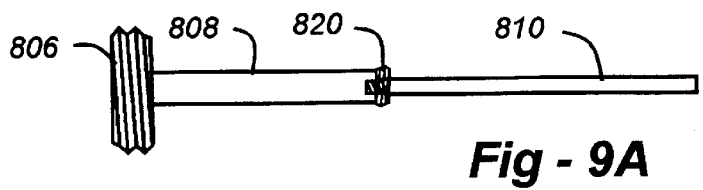
*Fig - 9A*
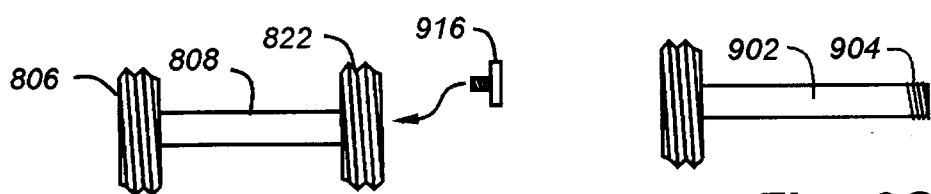
*Fig - 9B*          *Fig - 9C*
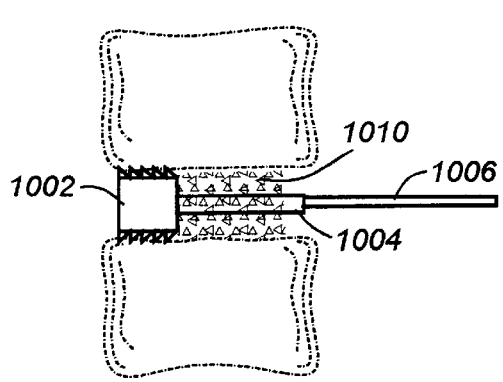          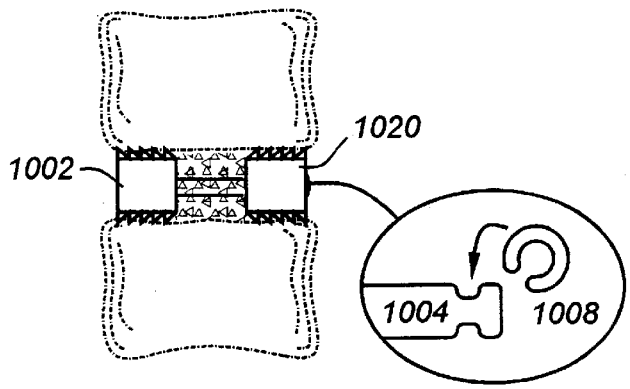
*Fig - 10A*          *Fig - 10B*
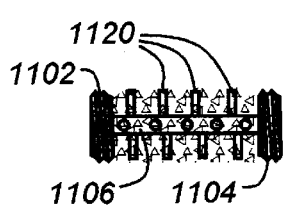          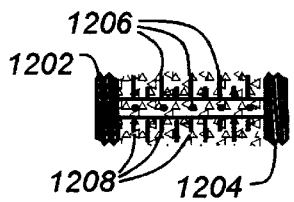
*Fig - 11*          *Fig - 12*

US 6,494,883 B1

BONE REINFORCERS

FIELD OF THE INVENTION

The present invention relates generally to orthopedic surgery and, in particular, to interbody cages and dowels of the type for use in interbody spinal fusions.

BACKGROUND OF THE INVENTION

With respect to spinal surgery wherein one or more vertebrae are fused, the use of bone dowels have certain advantages over metal cages. First, allograft bone readily fuses to the vertebrae. Second, it is often impossible to determine if metal bone-filled cages have fused to adjacent vertebrae, because the metal obstructs x-ray imaging of the bone within the metal cages as well as the cage vertebra junction. Third, bone dowels have a modulus of elasticity closer to that vertebrae. Consequently, bone dowels stress shield less than metal cages.

Bone dowels have certain disadvantages when compared to metal cages, however. Allograft bone incorporates into host bone through a process known as "creeping substitution." Host blood vessels grow into the allograft bone in the first stage of this process. Bone removing cells known as osteoclasts then invade the allograft bone. After sufficient bone is removed by the osteoclasts, bone building cells known as osteoblasts lay down new host bone on the allograft bone.

This remodeling process may go on for years. As would be expected, the allograft is weakened by the channels formed by the blood vessels, as well as the bone removal by the osteoclasts. Although the allograft regains its strength once sufficient new bone is formed, allograft bone dowels are at risk of fracture during the period of time that they are weakened. Allograft bone dowel fracture is well known to those skilled in the art of spinal surgery. Bone dowels are also weaker than metal cages, even before they undergo creeping substitution. Consequently, bone dowels can fracture during surgical placement. Fractured dowels can be difficult to remove, and may lead to failure of a fusion to occur. The properties of bone also do not allow certain shapes or machining.

SUMMARY OF THE INVENTION

This invention improves upon existing bone dowels through the use of rigid, preferably metallic end plates, thereby providing the advantages of bone dowels while eliminating the disadvantages, as discussed above. The plates are positioned relative to the anterior and posterior end surfaces of the bone dowel, which may be an existing, modified, or a specially fabricated bone section.

The completed structure may be inserted, removed, and positioned into the vertebrae in the same manner as existing devices, that is, by way of a threaded or frictional fit. However, the use of the rigid endplates facilitates load sharing which helps to prevent graft fracture.

In the preferred embodiment, the end plates are positioned against the end surfaces of the bone section through the use of a link member, which passes through the interior of the bone section and connects the end plates. One of the end plates may include a threaded bore, and one end of the link member may be threaded to receive the threaded bore of that end plate to hold it in place. The use of a link member allows a plurality of bone sections to be journaled onto the link member, with a disk of rigid, preferably metallic material to be interposed between each bone section.

Alternatively, the end surfaces of the bone section may each include an aperture having an inside diameter, with each end plate having an outside diameter corresponding to the inside diameter of the apertures, enabling the end plates to be positioned against the end surfaces of the bone section through a frictional fit.

At least the bone section preferably includes an exterior threading, such that with a generally cylindrical outer shape the finished structure may be screwed into place. Alternative geometries, including rectangular, trapezoidal, and so forth may also be accommodated, with and without exterior threading or serrading.

BRIEF DESCRIPTION OF THE DRAWINGS

FIG. 8A is a side-view drawing depicting an alternative method according to the invention wherein a bone reinforcer is assembled within an intervertebral disc space as opposed to being inserted as a finished component;

FIG. 8B is a drawing which shows a progression which began with reference to FIG. 8A;

FIG. 8C continues the progression of FIGS. 8A and 8B, with the addition of an end-cap;

FIG. 8D shows the assembled reinforcer using the steps of FIGS. 8A–8C;

FIG. 8E is a side-view drawing which shows how multiple disc spacers may be added during an in situ assembly;

FIG. 9A is a drawing of an extension post used in assembling a bone-reinforcer within a disc space;

FIG. 9B is a drawing which shows how an end-cap may be fastened to a central member such as a circular rod;

FIG. 9C is a drawing of an alternative embodiment wherein a reverse thread is used as opposed to a separate fastener with respect to an end plate;

FIG. 10A is a side-view drawing of an alternative impacted embodiment assembled within a disc space;

FIG. 10B is a side-view drawing of a completed structure according to the practice of FIG. 10A, showing, in particular, the use of a retaining clip;

FIG. 11 is a side-view drawing of an alternative embodiment of the invention wherein a central member includes projections which holds loose bone graft material in position;

FIG. 12 is a side-view drawing of yet a further different alternative embodiment of the invention, wherein spikes of different length are used for the purpose of holding bone graft and for holding the completed structure within place within an intervertebral space;

DETAILED DESCRIPTION OF THE INVENTION

Figure 1:
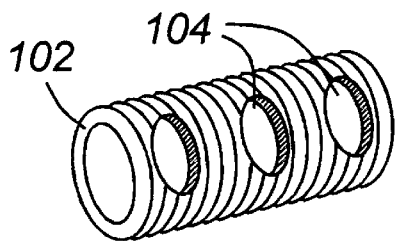
FIG. 1 is an isometric view of a prior-art threaded cylindrical metal cage.
Figure 2:
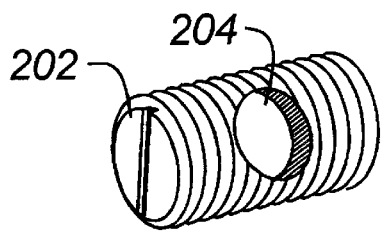
FIG. 2 is an isometric view of a prior-art cylindrical, threaded bone dowel.

FIGS. 1 and 2 are perspective-view drawings of existing interbody fusion devices, with FIG. 1 being rendered in the form of a metal cage, and FIG. 2 being implemented in the form of a bone dowel. In both cases, the bodies 102 and 202 include respective apertures 104 and 204 to receive bone graft material to enhance fusing. The use of an all-metal component has its disadvantages, as does the use of an all-bone component as discussed above with respect to the background of the invention, such that those sufficiencies will not be repeated here. Broadly, the instant invention combines the judicious use of metal and bone components in reinforcers of this type, to gain the advantages of using both materials while avoiding the disadvantages.

Figure 3:
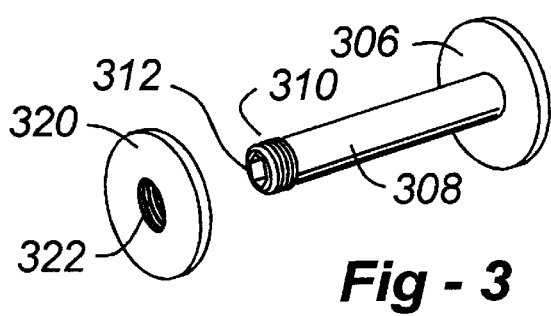
FIG. 3 is a perspective, exploded view drawing of certain components associated with one embodiment of the invention.

FIG. 3 is an exploded view drawing of certain components of the invention, which are preferably fabricated from a biocompatible metal, metallic component or alternative material sufficient to impart strength to the finished article. The components in this case include an end plate 306 having attached thereto a rod of smaller diameter 308, terminating in a threaded end 310, preferably further including a recess 312 to receive a tool such as an alien wrench, screwdriver, and so forth, to be used for stabilization and/or tightening.

Onto the threaded end 310, there is received a second outer plate 320 having threads 322 which mate with the threads 310. These are preferably reverse threads, so that they tighten rather than loosen when the device is installed. Although the rod 308 is shown preferably permanently connected to the end plate 306, it will be appreciated that a threaded, preferably reverse-threaded connection may be provided there as well.

Figure 4:
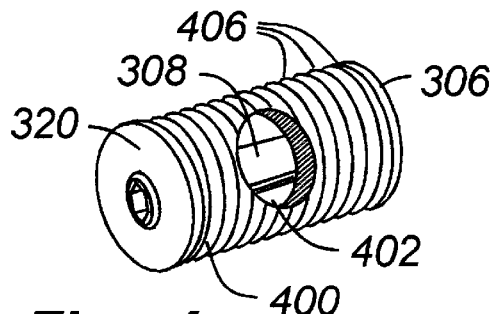
FIG. 4 is an isometric view of the embodiment of FIG. 3 in an assembled form.

FIG. 4 is a drawing which shows how the components of FIG. 3 are assembled to produce a finished reinforcer according to the invention. Broadly, the end plates 306 and 320 are spaced apart when assembled to provide a spacer therebetween to receive a section of bone grating material 400 preferably including one or more apertures 402 to receive bone graft material sufficient to enhance fusion. Note that the threads 406 on the device overall are forwardly oriented, such that, by placing an appropriate tool into the aperture 322, the plug may be rotated into place without the threaded connection(s) of the end plates becoming loose.

Figure 5A:
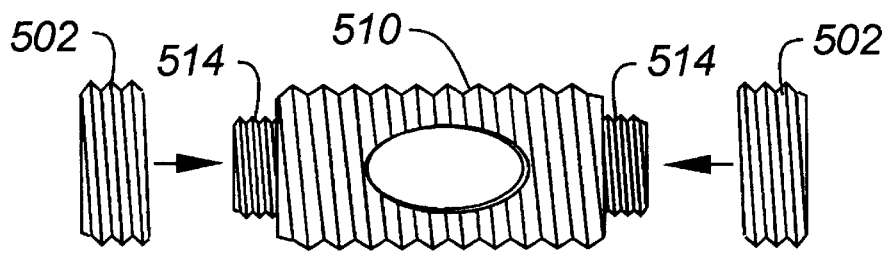
FIG. 5A is an exploded-view drawing depicting an alternative embodiment of the invention having threaded end sections.
Figure 5B:
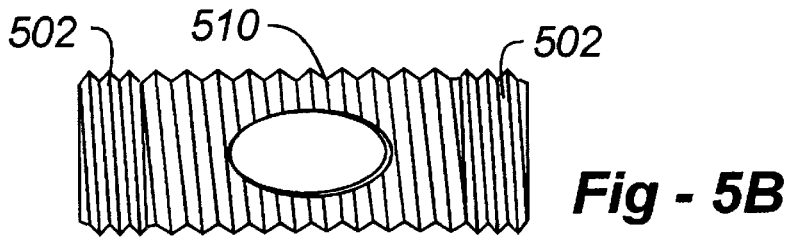
FIG. 5B is a drawing of a completed assembly according to the invention of FIG. 5A.

FIGS. 5A and 5B represent an alternative embodiment of the invention, wherein rigid discs 502, preferably of metal, having inner threads enabling them to be rotated onto a dowel 510 of bone material having threaded end sections 514 and one or more apertures 512. The end plates 502 are rotated onto the end sections 514 of the dowel 510, preferably until they become flush with the body of the dowel, as shown in FIG. 5B. Note that since the end plates are preferably tightened against the ends of the dowel, forward or reverse threads may alternatively be used for such purpose.

Figure 6A:
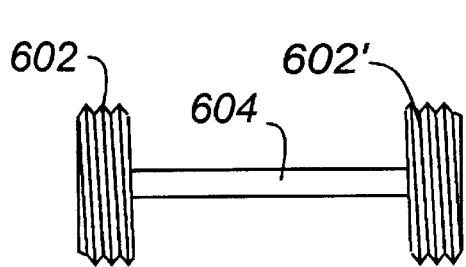
FIG. 6A is an end component associated with an alternative embodiment of the invention.
Figure 6C:
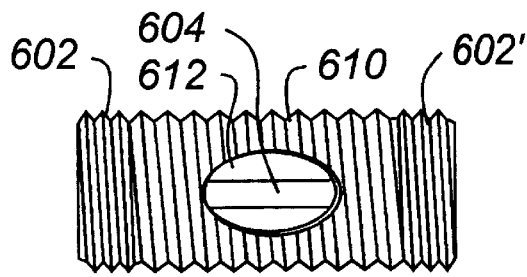
FIG. 6C is a drawing of a completed assembly according to the invention of FIGS. 6A and 6B.
Figure 6B:
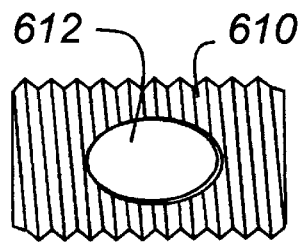
FIG. 6B is a progression of the embodiment of the invention introduced to with respect to FIG. 6A.

FIGS. 6A–6C illustrate a different embodiment of the invention, which may be used to produce finished articles of various shapes, including cylindrical, rectangular, trapezoidal, and other geometries. As shown in FIG. 6A, the structure includes two end pieces 602 and 602', these being attached with a member 604 so that they are spaced apart from one another by an appropriate distance to receive the bone section 610 having one or more apertures 612 illustrated in FIG. 6B. In this case, it is noted that, as opposed to a helical thread disposed on the outer body of the device, teeth are provided on one or more opposing surfaces, such that the device is tapped into place as opposed to being rotatably inserted, thereby enabling the shape to non-circular in cross-section. FIG. 6C shows the completed structure, with the insert of FIG. 6B being installed onto the supports shown in FIG. 6A.

Although the embodiments so far described generally illustrate two end plates separated from one another having a bone insert therebetween, the invention is not limited as to the number of plates or spacers, and may use intermediate discs or rings along the body of the device. FIG. 7E is a drawing which shows such a finished article generally at 730, having at least one non-bone spacer along the length of the device.

Figure 7A:
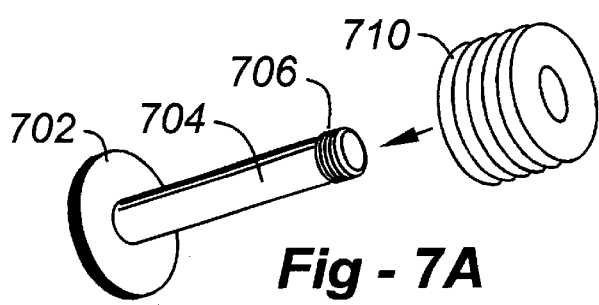
FIG. 7A begins a sequence of drawings showing how multiple bone dowels and plates may be stacked to provide a further alternative embodiment of the invention.
Figure 7B:
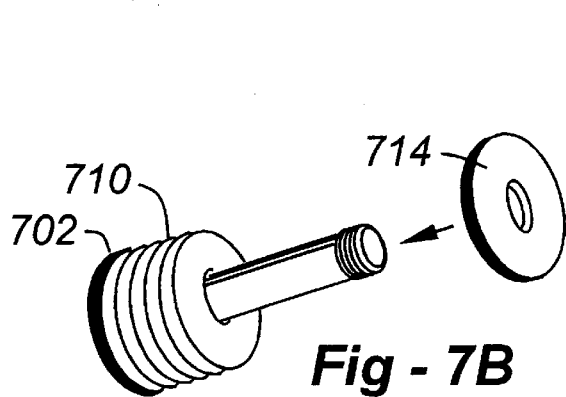
FIG. 7B shows the stacking of a first bone dowel and the receipt of a first end plate.
Figure 7D:
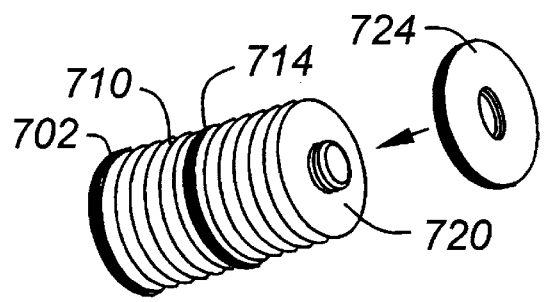
FIG. 7D shows the receipt of an end plate.
Figure 7C:
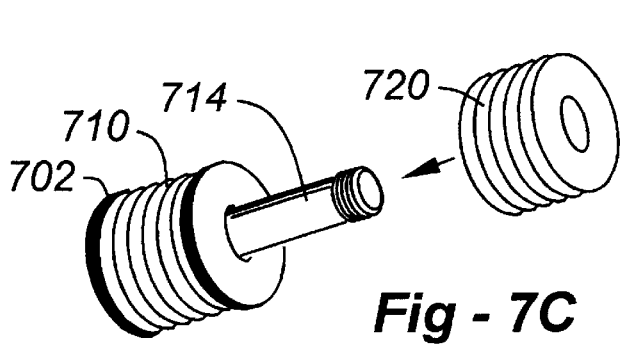
FIG. 7C shows the receipt of a second bone dowel.
Figure 7E:
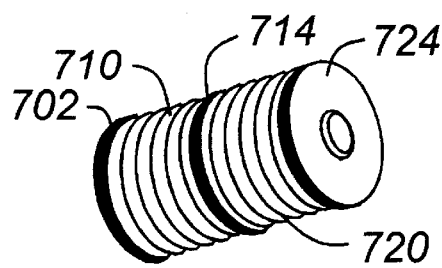
FIG. 7E is a drawing which illustrates a completed stacked structure according to a further alternative embodiment of the invention.

FIGS. 7A–7D show how such a device would preferably be assembled, namely beginning with a first plate 702 coupled to a rod 704 having a threaded end 706, a first section of bone material 710 would be journaled onto the rod 704, as shown in FIG. 7A. A second non-bone ring 714 would then be added, as shown in FIG. 7B, followed by a second piece of bone 720, as shown in FIG. 7C. A final end plate 724, having an internal threaded bore which cooperates with the threaded end 706 of the rod 704 would then be added, as shown in FIG. 7B, to achieve the finished structure shown in FIG. 7E, generally at 730.

It will be appreciated by one of skill in the art, that more than two or three non-bone spacers may be used in any of the embodiments shown herein, and that autograft or all graft bone may be used, that is, bone from the same patient or a different individual. For that matter, synthetic bone material may be used as opposed to naturally occurring bone and, in addition to threaded connections between the various components, alternative assembly techniques such as compression or force-fit interfaces may be used.

Although the embodiments described thus far reside in completed reinforcers which are inserted into an intervertebral disc space, the invention is not limited to prefabricated structures, but, in fact, devices according to the invention may be assembled progressively within the disc space. FIGS. 8A–8D illustrate such a sequence of assembly, with FIG. 8E being used to show that multiple spacer plates in addition to the end plates may also be assembled in situ. In these figures, a bone reinforcer is being assembled in the disc space between upper and lower vertebrae 802 and 804, respectively.

The installation procedure may be carried out from an anterior or posterior approach. Assuming the latter, an anterior end plate 806 attached to a distal rod portion 808 is first installed, by pushing the end piece 806 into position using a detachable extender rod 810. To ensure that insertion progresses in a well-defined and controlled manner, an alignment sleeve 812 may temporarily be used as a guide. Having placed the anterior end piece, bone graft 820 is packed into the space around the rod 808, and a posterior end piece 822 is installed onto the assembly over extension 810. FIG. 8C shows the posterior end plate in position, at which time the extension piece 810 is removed, as shown in FIG. 8D, leaving only the bone graft material surrounding a central member connecting the two end plates 806 and 822.

As with other embodiments described herein, the invention is not limited to the use of rigid end pieces, but rather, intermediate discs or rigid elements may be used, including embodiments wherein the device is assembled within the disc space. Once such configuration is shown in FIG. 8E, wherein multiple plates 850 are used, with bone graft 852 being progressively added as each plate is installed.

FIGS. 9A–9C illustrate ways in which the extension member 810 may be removed, and the posterior end plate installed. FIG. 9A shows the anterior end plate 806, preferably rigidly attached to the central member 808, with extender 810 being attached thereto, along with the addition of normal or forward-oriented threads 820 located at the posterior terminating end of the member 808. Having removed the extender 810, the posterior end plate 822 may be installed through the use of a locking screw 916 having reversed threads from that of 820, to ensure that the last to install end plate does not become loose when the locking screw 916 is tightened down. As an alternative, the threads 820 may be reverse-oriented, as shown in FIG. 9C, in which case the end piece may be screwed on without the need for an addition locking screw or other mechanism.

FIG. 10A illustrates a different alternative embodiment of the invention, wherein, as opposed to relatively thin end pieces, impactor plugs such as 1002 and 1020 are instead utilized. FIG. 10A illustrates the initial steps associated with the introduction of this assembly, with the anterior plug 1002 being forced into place, and bone graft material being added around the central member 1004. Again, an alignment rod 1006 is preferably temporarily used for placement. As shown in FIG. 10B, the second end plug 1020 is impacted into place over the central member 1004, at which time the alignment rod is removed. Since, in this embodiment, spiked or otherwise roughened superior and anterior surfaces are used on the plugs 1002 and 1020, a simplified retainer clip such as 1008 may be received by a corresponding groove in the central member 1004, as shown in the enlarged view. Although the plugs 1002 and 1020 may be circular in cross-section, in this particular embodiment they are preferably rectangular in cross-section, allowing a larger surface area for superior and inferior end plate engagement.

FIGS. 11 and 12 illustrate other alternative embodiments of the invention, including the use of spikes or rod emanating from the central member between the end pieces or intermediate pieces. Such a configuration may be used with prefabricated components according to the invention or, alternatively, assembled in place between the disc space. In FIG. 11, two end plates 1102 and 1104 are used, though others may be added lengthwise along the central member 1106, but from the member 1106, protrusions 1120 are provided. Depending upon their composition, and strength, the protrusions 1120 may provide additional support along the length of the reinforcer, but in addition, the protrusions 1120 act to hold the bone graft material in place, thereby further enhancing fusion.

Although the protrusions such as 1120 shown in FIG. 11 may be uniform in length as measured from the central member connecting the end plates or intermediate pieces, as shown in FIG. 12, protrusions could also be used which are collectively wider in cross-section than the intervertebral space, such that, during insertion, they are bent down and engage with the end plates, thereby preventing the completed structure from backing out while, at the same time, holding the bone graft material in position. These longer protrusions such as 1206, may be used in combination with shorter protrusions 1208, with the shorter protrusions being specifically intended to hold the bone graft material in place, while the longer protrusions act as barbs to hold the overall structure in position.

Figure 13A:
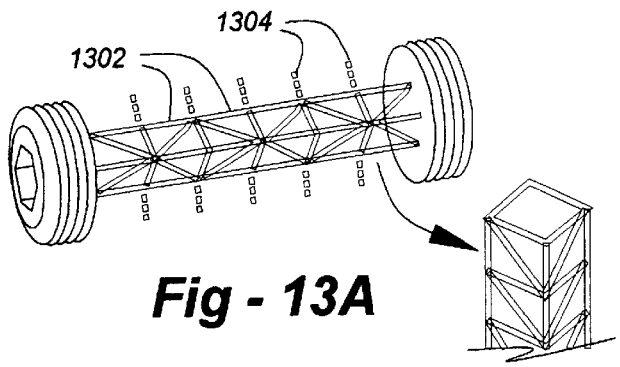
FIG. 13A is a drawing which shows yet a further, different alternative embodiment of the invention, wherein a central member used to connect end plates is itself open through the use of multiple structural members.
Figure 13B:
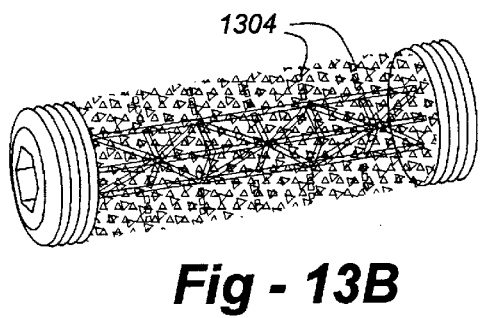
FIG. 13B is a drawing which shows the device of FIG. 13A with bone-graft material packed in and around the central member.
Figure 14A:
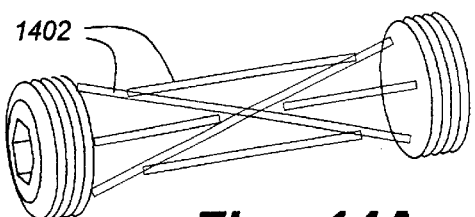
FIG. 14A illustrates a way in which multiple struts may be used, each terminating at both end plates.

As opposed to a solid central member connecting end plates, multiple structural members 1302 may be used for an open core, as shown in the threaded embodiment of FIG. 13A. In conjunction with these cross-members, which may be arranged much like those found on a radio tower, optional spikes 1304 may be used to help hold bone graft into position, as shown in FIG. 13B. As a further alternative arrangement, the multiple struts may go from end section to end section, as shown in the threaded embodiment of FIG. 14A.

Figure 14B:
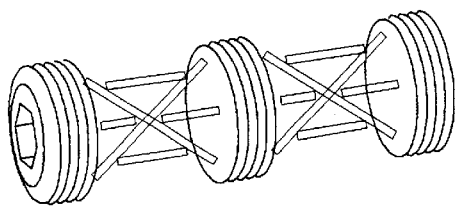
FIG. 14B illustrates the use of multiple struts with one or more intermediate spacers.
Figure 15A:
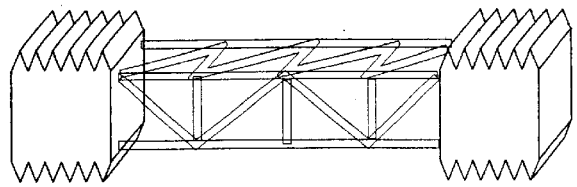
FIG. 15A is a drawing which shows the use of multiple structural members between end sections in an impacted, as opposed to threaded, embodiment.
Figure 15B:
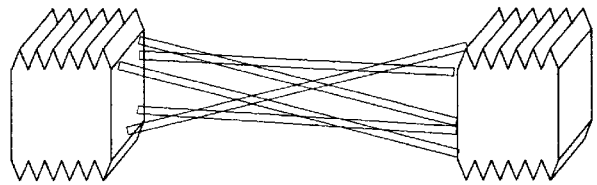
FIG. 15B is a drawing of an impacted embodiment wherein multiple struts are used lengthwise between the end sections.
Figure 15C:
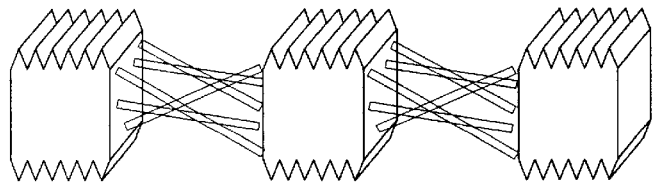
FIG. 15C is a drawing which shows an impacted embodiment of the invention having an intermediate member, again interconnected with multiple struts.

Intermediate spacers may be used in all of these embodiments, including those which use multiple struts 1402, as shown in FIG. 14B. In addition, the use of multiple longitudinal and cross-braced struts may also be applied to impacted embodiments, with or without central spacers, as shown in FIGS. 15A–15C. The connecting struts may have an orientation that is wider in an anterior-to-posterior dimension than the superior-to-inferior dimension to keep the struts further from the end plate of the vertebrae, thereby allowing for an easier determination of fusion through x-ray analysis. The strut embodiments may also help to hold cancellous bone, which may be packed between and over the struts prior to insertion.

I claim:

1. A reinforced bone plug, comprising:
   a mid section formed from a piece of natural or synthetic bone having opposing ends; and
   a pair of rigid, non-bone end plates, each positioned against a respective end of the mid section.

2. The reinforced bone plug of claim 1, wherein the end plates are at least partially metallic.

3. The reinforced bone plug of claim 1, including at least one link member that passes through the mid section so as to interconnect the opposing ends.

4. The reinforced bone plug of claim 3, wherein:
   one of the end plates includes a threaded bore; and one end of the link member is threaded to receive the threaded bore of that end plate.

5. The reinforced bone plug of claim 1, further including:

a plurality of mid sections; and a disk of rigid material disposed between each mid section.

6. The reinforced bone plug of claim 1, wherein the mid section includes cancellous bone.

7. The reinforced bone plug of claim 1, wherein the mid section includes cortical bone.

8. The reinforced bone plug of claim 1, wherein:

each end of the mid section includes an aperture having an inside diameter;

each end plate includes a feature having an outside diameter corresponding to the inside diameter of the apertures; and wherein the end plates are positioned against the end surfaces of the bone mid section through a frictional fit between the inside and outside diameters.

9. The reinforced bone plug of claim 1, wherein the ends of the bone mid section are threaded to receive the end plates.

10. The reinforced bone plug of claim 1, wherein the mid section in combination with the end plates assumes a generally cylindrical, threaded configuration permitting a screw-in installation.

11. The reinforced bone plug of claim 1, wherein the mid section in combination with the end plates assumes a configuration suitable to an impacted installation.

12. The reinforced bone plug claim 1, wherein at least the mid section includes serrading or protrusions to hold the plug in position once installed.

* * * * *